United States Patent
Pires et al.

(10) Patent No.: US 9,927,419 B2
(45) Date of Patent: Mar. 27, 2018

(54) SAMPLE TESTING APPARATUS AND METHOD

(71) Applicant: Wellstream International Limited, Newcastle-Upon-Tyne (GB)

(72) Inventors: Fabio de Souza Pires, Newcastle-Upon-Tyne (GB); Fabio Pinheiro dos Santos, Newcastle-Upon-Tyne (GB)

(73) Assignee: GE Oil & Gas UK Limited, Nailsea, Bristol (GB)

( * ) Notice: Subject to any disclaimer, the term of this patent is extended or adjusted under 35 U.S.C. 154(b) by 960 days.

(21) Appl. No.: 13/919,532

(22) Filed: Jun. 17, 2013

(65) Prior Publication Data
US 2013/0340542 A1 Dec. 26, 2013

(30) Foreign Application Priority Data
Jun. 26, 2012 (EP) .................. 12173648

(51) Int. Cl.
*G01N 33/20* (2006.01)
*G01N 17/04* (2006.01)
*G01N 3/32* (2006.01)

(52) U.S. Cl.
CPC .............. *G01N 33/20* (2013.01); *G01N 3/32* (2013.01); *G01N 17/046* (2013.01);
(Continued)

(58) Field of Classification Search
CPC .... E21B 17/012; E21B 17/015; F16L 11/083; F16L 57/00; G01M 3/2807;
(Continued)

(56) References Cited

U.S. PATENT DOCUMENTS 6,792,357 B2 * 9/2004 Menon et al. .................. 702/27
8,033,164 B2 * 10/2011 Dermody ............ G01N 17/043
422/53
(Continued)

FOREIGN PATENT DOCUMENTS

CN 101900663 12/2010
EP 2 352 007 A1 8/2011

OTHER PUBLICATIONS

Rubin et al.: "Qualification of Steel Wire for Flexible Pipes", Corrosion NACEXPO 2006, 61st Annual Conference and Exposition, 2006; XP008156563, 20 pages.*
(Continued)

*Primary Examiner* — Hezron E Williams
*Assistant Examiner* — Gedeon M Kidanu
(74) *Attorney, Agent, or Firm* — Myers Bigel, P.A.

(57) ABSTRACT

A test apparatus (12) and a method of testing a sample (30) are disclosed. The method comprises receiving a test sample (30) within a test chamber (14), the test chamber (14) containing two or more iron saturation elements (2) separated by a spacer (16); and filling the test chamber (14) with a test solution, the iron saturation elements (2) being arranged to saturate the test solution with iron. Each iron saturation element (2) is shaped such that it has a predetermined surface area such that the ratio of the volume of the test solution to the surface area of the iron saturation elements (2) and the test sample (30) exposed to the test solution can be calculated.

11 Claims, 3 Drawing Sheets

(52) U.S. Cl.
CPC ............... *G01N 2203/0023* (2013.01); *G01N 2203/024* (2013.01); *G01N 2203/0464* (2013.01)

(58) Field of Classification Search
CPC .. G01N 17/046; G01N 2203/024; G01N 3/20; G01N 17/002; G01N 2203/0023; G01N 2203/0296
USPC ......... 73/53, 61, 86, 87, 104, 760, 799, 819, 73/856, 859; 436/6; 422/53
See application file for complete search history.

(56) References Cited

U.S. PATENT DOCUMENTS

| | | | |
|---|---|---|---|
| 8,513,020 B2* | 8/2013 | Hehn | G01N 3/20 422/53 |
| 2009/0158827 A1* | 6/2009 | Dermody | G01N 17/043 73/86 |
| 2011/0136239 A1* | 6/2011 | Hehn | G01N 3/20 436/6 |

OTHER PUBLICATIONS

Clements et al.: "An analysis of the effect of frequency, environment, materials variations and test modes in corrosion fatigue testing of flexible pipe armour wires", International Corrosion Conference Series; Corrosion 2012, National Association of Corrosion Engineers, US; Salt Lake City, UT, USA, vol. 6, Jan. 1, 2012, pp. 4929-4940; XP008156644, ISSN: 0361-4409.
Extended European Search Report corresponding to European Patent Application No. 12173648.2; dated Nov. 28, 2012; 9 pages.
Rubin et al.: "Qualification of Steel Wire for Flexible Pipes", Corrosion NACEXPO 2006, 61$^{st}$ Annual Conference and Exposition, 2006; XP008156563, 20 Pages.
Taravel-Condat et al.: "Qualification of high strength carbon steel wires for use in specific annulus environment of flexible pipes containing CO2 and H 2S", Proceedings of the 25$^{th}$ International Conference on Offshore Mechanics and Arctic Engineering—2006: Presented at the 25$^{th}$ International Conference on Offshore Mechanics and Arctic Engineering; Safety and Reliability; Materials Technology; Douglas, vol. 3, Jan. 1, 2006, pp. 585-591, XP008156653, ISBN: 0-7918-4748-9.
Berge et al., "Environmental Effects on Fatigue Strength of Armour Wire for Flexible Risers," Proceedings of OMAE 2008, 27$^{th}$ Int. Conf. Offshore Mechanics and Arctic Engineering, Estoril, Portugal, Jun. 2008, 8 pages.
Office Action for Chinese Patent Application No. 201310260122.X dated Nov. 10, 2016, original and translation, 9 pages.

* cited by examiner

SAMPLE TESTING APPARATUS AND METHOD

RELATED APPLICATION

The present application claims priority under 35 U.S.C. § 119 to European Patent Application No. EP12173648.2, filed 26 Jun. 2012 in the European Patent Office, the disclosure of which is incorporated herein by reference in its entirety.

The present invention relates to a testing apparatus and a method of testing a sample. In particular, but not exclusively, the present invention relates to a method and apparatus for performing corrosion or corrosion fatigue testing on samples of armouring wire used to construct a flexible pipe.

Traditionally flexible pipe is utilised to transport production fluids, such as oil and/or gas and/or water, from one location to another. Flexible pipe is particularly useful in connecting a sub-sea location (which may be deep underwater, say 1000 meters or more) to a sea level location. The pipe may have an internal diameter of typically up to around 0.6 meters. Flexible pipe is generally formed as an assembly of a flexible pipe body and one or more end fittings. The pipe body is typically formed as a combination of layered materials that form a pressure-containing conduit. The pipe structure allows large deflections without causing bending stresses that impair the pipe's functionality over its lifetime. The pipe body is generally built up as a combined structure including metallic and polymer layers.

In many known flexible pipe designs the pipe body includes one or more pressure armour layers. The primary load on such layers is formed from radial forces. Pressure armour layers often have a specific cross section profile to interlock so as to be able to maintain and absorb radial forces resulting from outer or inner pressure on the pipe. The cross sectional profile of the wound wires which thus prevent the pipe from collapsing or bursting as a result of pressure are sometimes called pressure-resistant profiles. When pressure armour layers are formed from helically wound wire forming hoop components, the radial forces from outer or inner pressure on the pipe cause the hoop components to expand or contract, putting a tensile load on the wires.

In many known flexible pipe designs the pipe body includes one or more tensile armour layers. The primary loading on such a layer is tension. In high pressure applications, such as in deep and ultra deep water environments, the tensile armour layer experiences high tension loads from a combination of the internal pressure end cap load and the self-supported weight of the flexible pipe. This can cause failure in the flexible pipe since such conditions are experienced over prolonged periods of time.

Unbonded flexible pipe has been used for deep water (less than 3,300 feet (1,005.84 meters)) and ultra deep water (greater than 3,300 feet) developments. It is the increasing demand for oil which is causing exploration to occur at greater and greater depths where environmental factors are more extreme. For example in such deep and ultra-deep water environments ocean floor temperature increases the risk of production fluids cooling to a temperature that may lead to pipe blockage. Increased depths also increase the pressure associated with the environment in which the flexible pipe must operate. As a result the need for high levels of performance from the pressure armour and tensile armour layers of the flexible pipe body is increased.

One way to improve the load, response and thus performance of armour layers is to manufacture the layers from thicker and stronger and thus more robust materials. For example for pressure armour layers in which the layers are often formed from wound wires with adjacent windings in the layer interlocking, manufacturing the wires from thicker material results in the strength increasing appropriately. However, as more material is used the weight of the flexible pipe increases. Ultimately the weight of the flexible pipe can become a limiting factor in using flexible pipe. Additionally manufacturing flexible pipe using thicker and thicker material increases material costs appreciably, which is also a disadvantage.

During operation, production fluids are transported along an inner bore of the flexible pipe. These production fluids may contain, or comprise, gas. If an inner fluid retaining layer used to contain the fluids permits such gas to permeate there through, the gas can collect within the layers of the flexible pipe body. Generally speaking, the fluid retaining layer is composed of a material that prevents outward migration of production fluids. However, over time gas can slowly permeate through the fluid retaining layer and radially outwards into an annular region beyond the fluid retaining layer. The annular region extends to the next generally impermeable layer. The gas will tend to accumulate in the annulus region, and if this gas is not released, the build-up of pressure (over-pressurization of annulus gas) can cause failure of the flexible pipe. This is also a problem for flexible pipes that may be depressurized during use, i.e. when fluid is stopped from flowing through the pipe bore, which may occur for various reasons.

In addition, transportation of production fluids is known to often lead to various layers of the flexible pipe being subject to relatively acidic conditions. Such "sour" service is due to the migration of hydrogen sulphide ($H_2S$) along with other species, such as $CO_2$, from the internal bore of the pipe radially outwards. This is a result of some production fluids containing relatively high concentrations of hydrogen sulphide gas in solution or in gaseous form. Under such circumstances over time hydrogen sulphide and the other gas species such as $CO_2$ permeate through the fluid retaining layer into annulus regions defined between layers of the flexible pipe body. The $H_2S$ and $CO_2$ collect in these annular regions and gradually increase the acidity (reduce pH) of the environment in those regions. Metal components, for example the tapes forming the pressure armour layer and/or tensile armour layer in those annular regions, are thus subjected to acid enhanced corrosion, which, if not mitigated, could lead to extremely high corrosion rates and possibly failure. It will also be appreciated that end fittings potentially include many metallic component parts, and could equally be subjected to an acid environment.

Such a sour service environment can affect the overall performance of a flexible pipe over time. This can lead to a reduced lifetime expectation or even failure of the flexible pipe during use.

The complex cross section of an unbonded flexible pipe creates a challenging operating environment for carbon steel wires, which are typically used to form the armouring layers. In order to ensure that the armour layers can withstand the loads which are experienced in typical, and exceptional, operating conditions it is desirable to be able to model the characteristics of the operating environment within the annulus of a flexible pipe (the space between an inner polymer liner or barrier layer and an outer polymer sheath). Knowledge of the operating environment in the pipe annulus allows samples to be tested, for instance in corrosion fatigue tests under realistic conditions. As mentioned above, it is known that the annulus of a flexible pipe may be corrosive for carbon steel. Corrosion fatigue is fatigue in a corrosive environment. Carbon steel armouring wire is subject to corrosion fatigue due to mechanical degradation under the twin effects of corrosion and cyclic loading. Corrosion fatigue testing provides SN data curves where S is the magnitude of an applied stress and is plotted against a log scale of the number of cycles to failure N. Corrosion fatigue of armouring wire is a limiting factor in the design of flexible pipes. Conventional fatigue tests for armouring wire are performed in air and are liable to give a misleading indication of the strength of the armouring wire.

A. Rubin et al., "Qualification of Steel Wire for Flexible Pipes", Corrosion NACExpo 2006, 61$^{st}$ Annual Conference & Exposition, Paper 06149 presents work on predicting the fluid composition and pH of the annulus environment in unbonded flexible pipes. It also presents methods for testing corrosion fatigue in a simulation of a typical environment within a pipe annulus. While the structure of a flexible pipe is intended to ensure that the armouring wire is not brought into direct contact either with the surrounding sea water or the production fluid, the annulus environment is determined by the permeation of small molecules into the annulus from the production fluid (primarily $H_2O$, $CO_2$, $H_2S$ and $CH_4$) and also seawater ingress. In particular, the annulus environment may be corrosive due to the presence of water, $CO_2$ and $H_2S$. The annular space in a flexible pipe is primarily occupied with the armouring wires, resulting in a small free volume and a low ratio of free volume to steel surface area (V/S), for instance less than 0.1 ml/cm$^3$. It is known that with decreasing V/S, pH increases and the corrosion rate decreases in typical annulus environments.

Rubin et al. describes a developed test methodology for corrosion fatigue testing in a typical annulus environment. A four point bending test rig is used to apply load to samples of armouring wire. Each sample, comprising a length of wire substantially longer than its cross section dimensions, is supported towards either end on 35 mm diameter ceramic cylinders with polymer spacers between samples to prevent sideways movement. Two further ceramic cylinders apply the load to the mid part of the samples providing maximum loading between the two centre cylinders which can be measured using a strain gauge applied to the samples. The ceramic cylinders are secured at a spacing of 100 mm and a piston is provided to move the centre cylinders perpendicularly to the samples. The applied loading is arranged to give a constant ratio between minimum stress and maximum stress (R) with a target value for R of 0.1. The number of loading cycles is in excess of $10^5$ and applied stress is in the range 250 to 400 MPa. The loading frequency is typically 0.5 to 1 Hz. The samples are prepared to as accurately as possible recreate their condition in the operating environment.

The test rig described in Rubin et al. is fitted with a system to provide the required test environment, including an environmental test chamber surrounding the samples to be filled with a test solution. Precautions are taken to ensure that the test solution and the chamber are completely deaerated. Rubin et al. described tests conducted in artificial seawater or a 5% NaCl solution in water. The solution is saturated with a mixture of $H_2S$ and $CO_2$ as the test gas. This saturation of $H_2S$ and $CO_2$ recreates the typical environment in a pipe annulus where the low free volume for flooding and condensation is filled with an aqueous solution saturated with the contaminants which pass through the liner or barrier into the annulus. Steel wool is also added to the test environment to super saturate the aqueous test solution and attempt to simulate the water chemistry resulting from the V/S ratio in the pipe. The results reported by Rubin et al. demonstrate that corrosion rates in the annulus of flexible pipes is significantly lower than predicted by normal corrosion rate models. The pH is always above 5.5 and the liquid is oversaturated with iron. This suggests the ability to use thinner armouring wire.

S. Berge et al., "Environmental Effects of Fatigue Strength of Armour Wire for Flexible Risers", Proceedings of OMAE 2008, 27$^{th}$ Int. Conf. Offshore Mechanics and Artic Engineering, Estoril, Portugal, June 2008, OMAE2008-57132 presents a similar procedure for fatigue testing of armour wire in corrosive environments. Berge et al., describes the results of testing armouring wire in air and in aqueous environments with $H_2S$ and/or $CO_2$ at various partial pressures. A similar four point test rig is used with a gas tight vessel and a system for providing water a purging gas. Similarly to Rubin et al., Berge et al. describes controlling the test rig to ensure super saturation of Ferrous Iron ($Fe^{++}$) in the vessel. Iron saturation for both corrosion and corrosion-fatigue test solutions are widely used in the qualification of flexible pipe materials to simulate actual service conditions in which annulus fluid becomes supersaturated due to the low free volume. It is known that when a corrosive environment is iron saturated it becomes less severe and more representative of actual service conditions by increasing of the media pH and allowing the formation of protective scale layers on the armouring wire.

As described above, it is known when performing corrosion fatigue testing on samples of armouring wire to add steel wool to the test chamber to ensure that the test fluid is saturated with iron. A controlled, specified mass of steel wool is added to achieve the required iron saturation. However, as the diameter of the iron wool strings cannot be properly controlled, it is not possible to control the ratio between the total iron exposed area and the mass of iron added to the test media. Consequently, the free volume within the chamber cannot be accurately determined or controlled. This results in variation in the free volume to steel surface area ratio (V/S) for the sample away from typical annulus conditions reducing the applicability of measured corrosion fatigue data to real life situations and reducing the repeatability of experiments. Additionally, as the surface area of the steel wool is not known nor easily calculated with any degree of accuracy, the rate of iron saturation cannot be accurately predicted.

According to a first aspect of the present invention there is provided a test apparatus comprising: a test chamber arranged to be filled with a test solution and to receive a test sample; two or more iron saturation elements located within the test chamber to saturate the test solution with iron; and at least one spacer separating at least one pair of iron saturation elements; wherein each iron saturation element is shaped such that it has a predetermined surface area such that the ratio of the volume of the test solution to the surface area of the iron saturation elements and the test sample exposed to the test solution can be calculated.

Certain embodiments of the invention provide the advantage that the ratio of the volume of the test solution to the surface area of the iron saturation elements and the test sample exposed to the test solution can be accurately determined and controlled. This means that the test apparatus can accurately reproduce the operational conditions associated with the samples. For instance, when testing flexible pipe armouring wire samples, a very low ratio of free volume to steel surface area can be recreated. Additionally, certain embodiments of the invention provide a reliable way to saturate test solutions with iron at a controlled rate, allowing the repeatability of test conditions in different test setups.

At least some of the iron saturation elements may be formed from sheet material having a thickness that is less than the minimum width of the element in a direction perpendicular to the thickness direction.

The test apparatus may further comprise a support structure arranged to support at least two iron saturation elements and at least one spacer to form an iron saturation module.

The support structure may be arranged to support a variable number of iron saturation elements and spacers so as to adjust the ratio of the volume of the test solution to the surface area of the iron saturation elements and the test sample exposed to the test solution.

At least two iron saturation elements may be formed from a sheet material and have corresponding holes arranged to receive a guide rod of the support structure, and wherein the at least one spacer also comprises a hole arranged to receive the guide rod such that the spacer and the iron saturation elements are supported by the guide rod with the spacer between the iron saturation elements such that the test solution is in contact with first and second sides of the iron saturation elements surrounding the holes.

The test apparatus may further comprise a loading mechanism for applying tensile stress to the test sample within the test chamber.

The test apparatus may further comprise a first fluid inlet arranged to supply the test solution to the test chamber such that the volume of chamber surrounding the iron saturation elements and at least one spacer is substantially filled by the test solution.

The test apparatus may further comprise a second fluid inlet arranged to supply a test fluid to the test chamber.

The second fluid inlet may be arranged to supply $H_2S$ or $CO_2$ to the test chamber.

The iron saturation elements may be formed from carbon steel.

According to a second aspect of the present invention there is provided a method of testing a sample, the method comprising: receiving a test sample within a test chamber, the test chamber containing two or more iron saturation elements separated by a spacer; and filling the test chamber with a test solution, the iron saturation elements being arranged to saturate the test solution with iron; wherein each iron saturation element is shaped such that it has a predetermined surface area such that the ratio of the volume of the test solution to the surface area of the iron saturation elements and the test sample exposed to the test solution can be calculated.

According to a third aspect of the present invention there is provided a test apparatus substantially as herein described with reference to the accompanying drawings.

According to a fourth aspect of the present invention there is provided a method substantially as herein described with reference to the accompanying drawings.

Embodiments of the invention are further described hereinafter with reference to the accompanying drawings, in which.

In the drawings like reference numerals refer to like parts.

The present invention is based on the recognition that the problems experienced in the prior art associated with the use of steel wool to super saturate a test solution and to absorb free volume in corrosion fatigue testing can be addressed by using iron saturation elements having closely controlled shapes. By controlling the shapes of the iron saturation elements, the surface area, volume and mass of each element can be accurately determined. This allows the free volume to steel surface area ratio (V/S) within a test chamber to be accurately determined and controlled by varying the number of iron saturation elements used. The present invention also introduces the use of spacers between the iron saturation elements to maximise the exposed surface area of the elements.

The invention described herein uses steel or iron sheets or plates with different thicknesses and geometries to form iron saturation elements. The iron saturation elements have a controlled surface area in order to determine the surface area to mass ratio and the free volume to steel surface area ratio (V/S). An exemplary iron saturation element with one possible geometry is illustrated in FIG. 1.

Figure 1:
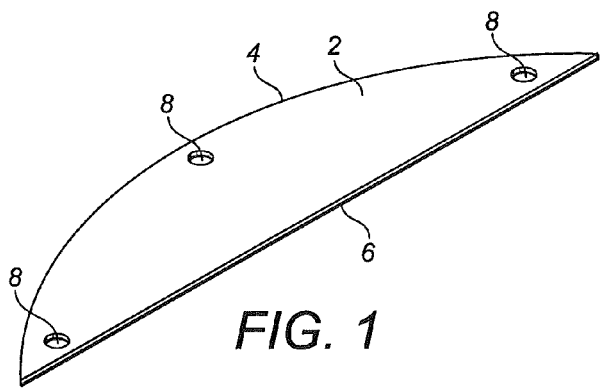
FIG. 1 illustrates an iron saturation element in accordance with an embodiment of the present invention.
Figure 5:
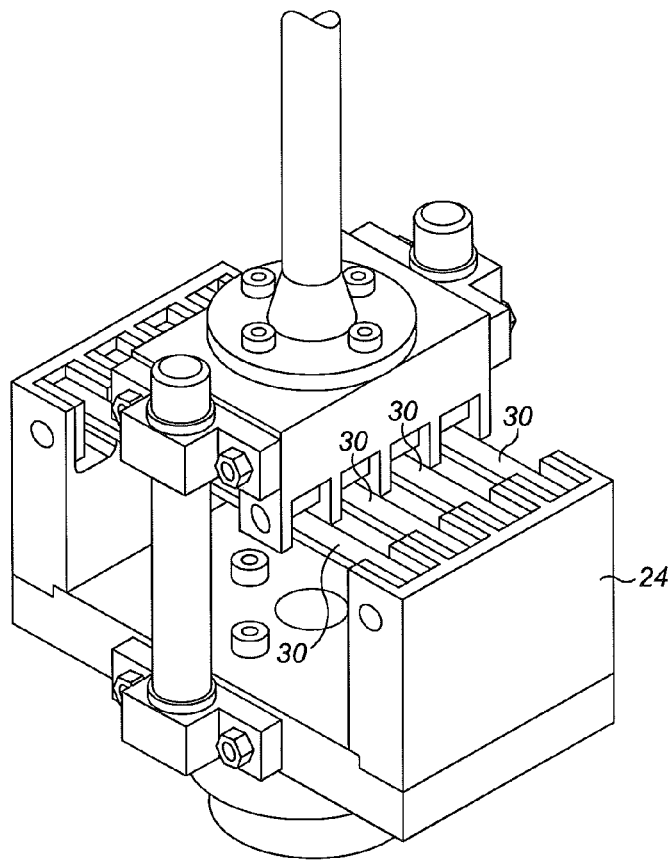
FIG. 5 illustrates a four point bending fatigue rig forming part of a test apparatus in accordance with an embodiment of the present invention.

FIG. 1 shows an iron saturation element 2 comprising a sheet of material curved on a first side 4 and straight on a second side 6. Each element 2 may be formed from carbon or alloy steel. The iron saturation element 2 includes three holes 8 arranged to receive guide rods 10 within a test apparatus 12 (shown in FIG. 6) for stacking multiple iron saturation elements 2. The iron saturation element 2 shown in FIG. 1 is generally shaped as a section of a circular plate which is relatively thin compared with the lengths of sides 4 and 6. Advantageously, forming the iron saturation elements 2 as thin plates ensures a large surface area relative to the mass and volume of the elements 2. The curved shape of the elements 2 is selected to fit the dimensions of a test chamber 14 within the test apparatus 12 (as will be described below in connection with FIGS. 5 and 6). However, it will be appreciated that the shape of element 2 may vary widely, including deviation from a plate structure, depending upon the particular shape and dimensions of a test chamber 14, and the requirements of a particular corrosion fatigue test. Furthermore, it will be appreciated that in a particular test apparatus 12 there may be a large number of elements 2, not all of which may be the same size and shape as each other depending upon the required ratios of mass, volume and surface area and general manufacturing limitations.

Figure 2:
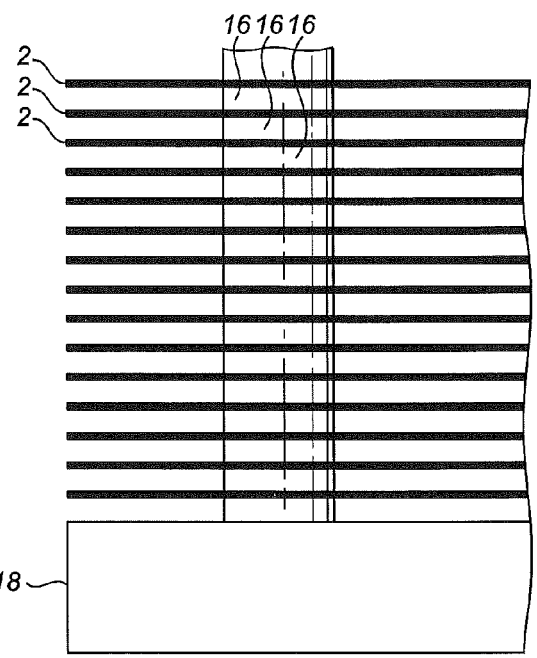
FIG. 2 illustrates a cross section of an arrangement of iron saturation elements and spacers in accordance with an embodiment of the present invention.

An important criterion for the elements 2 is that each element has an accurately determined surface area. By filling a test chamber 14 with elements 2 this means that the V/S ratio can be accurately controlled to be representative of conditions experienced in the annulus of a flexible pipe. Additionally, the rate of iron saturation within the test solution in chamber 14 can be controlled. It is important to ensure that the test solution can access as large a proportion of the surface area of each element 2 as possible, and also to ensure that the test solution fills the whole of the cavities between elements 2 such that the chamber 14 is fully deaerated. To allow this, the elements 2 are mounted in a support using spacers 16 to space the elements 2 apart, as shown in FIG. 2 which illustrates an enlarged portion of part of an iron saturation module 20. The spacers 16 are interleaved with the elements 2 so that no two elements 2 are in contact. The spacers may be formed from a polymeric or ceramic material. In one particularly preferred embodiment the guide rods 10 noted above are mounted on a solid base 18 and the elements 2 are passed over the guide rods 10 such that the guide rods 10 extend through holes 8. The spacers 16 may also be passed over the guide rods 10 in-between each pair of elements 2. The spacers 16 may thus comprise rings of material (such as spacers) having a central hole sized to receive rods 10.

It will be appreciated that depending upon the selected shape of elements 2 the support structure may vary. The purpose of the support structure is to ensure that the maximum area of the elements is in contact with the test solution. The size of the spacers 16 may also be varied to control the confinement ratio (the V/S ratio of the test apparatus). Thinner spacers 16 allow the addition of an increased surface area of iron to the test solution within the test chamber 14, and reduce the mass of carbon steel inside the test chamber 14. The control of the degree of confinement is an important feature for corrosion and corrosion-fatigue tests for flexible pipes components.

Figure 3:
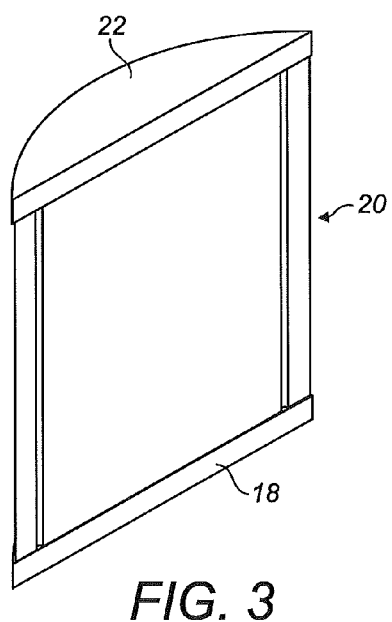
FIG. 3 illustrates an arrangement of iron saturation elements and spacers in accordance with an embodiment of the present invention.
Figure 4:
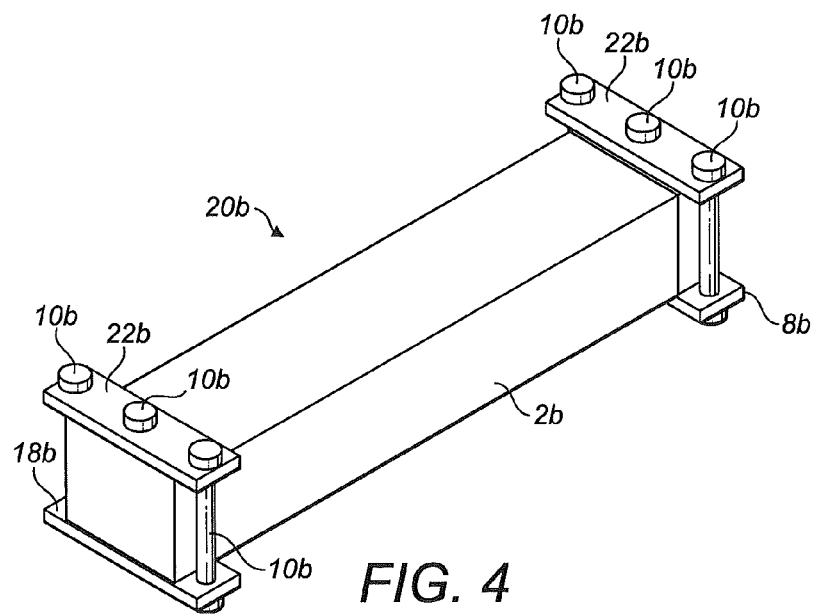
FIG. 4 illustrates an arrangement of iron saturation elements and spacers in accordance with an alternative embodiment of the present invention.
Figure 7:
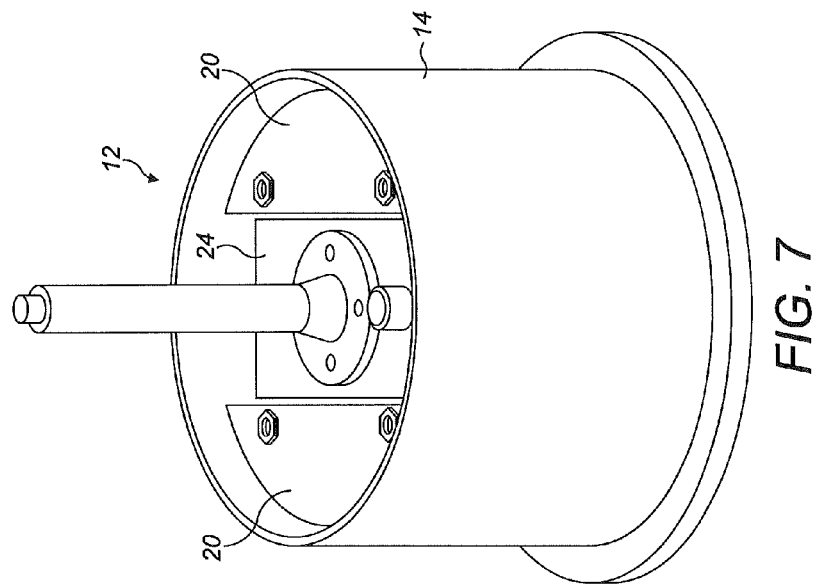
FIG. 7 illustrates the test apparatus of FIG. 6 fully assembled.
Figure 6:
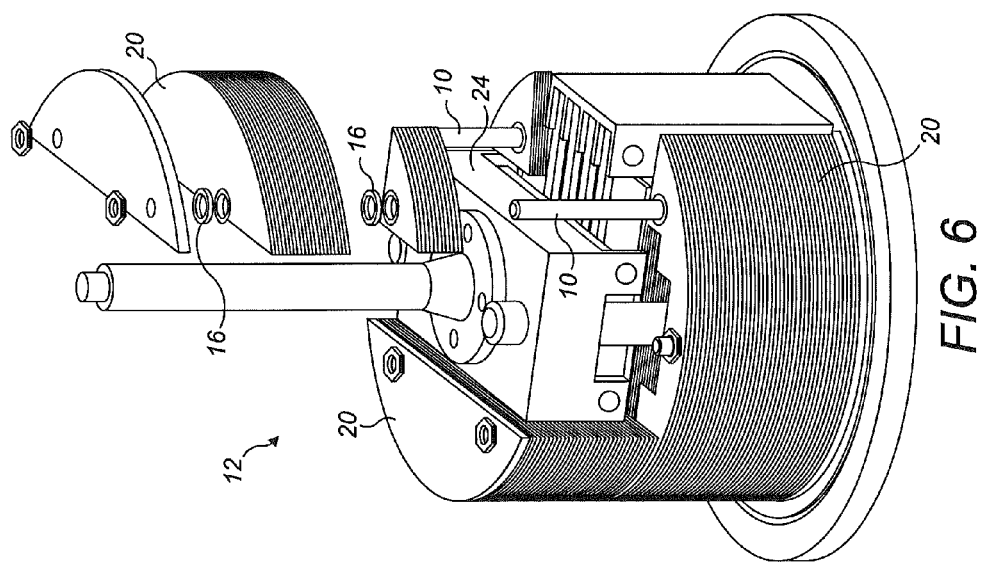
FIG. 6 illustrates a test apparatus in accordance with an embodiment of the present invention with the test chamber removed.

Once the required amount of iron saturation elements 2 is defined, as a function of the test requirements, the elements are assembled as illustrated in FIG. 2 in order to complete one module 20 of iron saturation elements 2 as shown in FIG. 3. FIG. 3 shows a plurality of elements 2 stacked between a base 18 and a top plate 22. The test apparatus 12 may use one or more iron saturation modules 20 to achieve the desired iron saturation of the test solution and the desired V/S ratio. For instance, FIGS. 6 and 7 illustrate a test apparatus 12 comprising a test chamber 14 (FIG. 7) illustrated in perspective view. The geometry of the iron saturation modules 20 may vary depending on the shape and dimensions of the test chamber 14. For instance FIG. 4 illustrates an alternative iron saturation module 20b having generally rectangular iron saturation elements 2b stacked and secured in position by top and bottom plates 22b, 18b at either end with external connecting guide rods 10b. Spacers (not visible in FIG. 4) separate each pair of adjacent iron saturation elements 2b.

It will be appreciated that the size and shape of each iron saturation module 10 will depend upon the size and shape of a particular test apparatus 12. For instance, FIGS. 6 and 7 illustrates a test apparatus 12 incorporating a plurality of saturation modules 20 shaped to fit about a four point bending fatigue rig 24 (also shown separately in FIG. 5). The four point bending fatigue rig is arranged to apply a bending force to one or more samples 30 and may be generally the same as described in the background section of the present specification and so will not be described in further detail. FIG. 6 shows the test apparatus 12 part way through assembly of the iron saturation modules, with the test chamber 14 removed. FIG. 7 shows the fully assembled test apparatus 12. It can be seen that the iron saturation modules 20 are positioned either side of the fatigue rig 24 and substantially take up the remainder of the volume of the test chamber 14. The test chamber 14 comprises a fluid vessel arranged to be filled with a test solution and arranged to be deaerated and supplied with $H_2S$ and $CO_2$ as described above in connection with the prior art.

Advantageously, the present invention provides a reliable way saturate a test solution within a corrosion fatigue test apparatus while accurately controlling the surface area to mass ratio of the iron added to the solution and accurately controlling the free volume to steel surface area ratio V/S for the test apparatus. This allows greater consistency across repeated experiments relative to existing test apparatuses in which steel wool is added to saturate the test solution with iron and to reduce the free volume. The confinement ratio (V/S) may be accurately controlled and arranged to be close to the confinement ratio within the annulus of an actual flexible pipe.

This methodology may be used in corrosion and corrosion fatigue tests for flexible pipe metallic armours, reproducing in a more controlled way the actual service conditions. Using existing testing methodologies in which the iron saturation and confinement ratio cannot be accurately controlled results in corrosion and corrosion fatigue measurements which are based on more severe environments the annulus environment experienced within an in-service flexible pipe. This has previously led to armouring wire being specified to a more exacting standard than is justified increasing the weight and cost of flexible pipes Various modifications to the detailed designs as described above are possible. As noted above, the precise shapes of the elements and the support structures may vary widely, so long as the selected shapes meet the requirements of a particular experimental setup.

The present invention has been described above in the context of experimentally test corrosion fatigue for armouring wire in flexible pipes, though it will be appreciated that the present invention is not limited to this. For instance, the iron saturation elements and support structures described above may be adapted for other experiments where it is necessary to recreate similar environmental conditions, for instance corrosion testing. Additionally, the present invention is applicable to testing other types of samples, for instance other components of a flexible pipe, or other unrelated components designed to operate in an iron saturated and/or confined environment.

With the above arrangement, the ratio of the volume of the test solution to the surface area of the iron saturation elements and the test sample exposed to the test solution can be easily and accurately calculated.

It will be clear to a person skilled in the art that features described in relation to any of the embodiments described above can be applicable interchangeably between the different embodiments. The embodiments described above are examples to illustrate various features of the invention.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A test apparatus comprising:
   a test chamber arranged to be filled with a test solution and to receive a test sample;
   two or more iron saturation elements located within the test chamber to saturate the test solution with iron; and
   at least one spacer separating at least one pair of iron saturation elements;
   wherein each iron saturation element is shaped such that it has a predetermined surface area such that the ratio of the volume of the test solution to the surface area of the iron saturation elements and the test sample exposed to the test solution can be calculated.

2. A test apparatus according to claim 1, wherein at least some of the iron saturation elements are formed from sheet material having a thickness that is less than the minimum width of the element in a direction perpendicular to the thickness direction.

3. A test apparatus according to claim 1, further comprising a loading mechanism for applying tensile stress to the test sample within the test chamber.

4. A test apparatus according to claim 1, further comprising a first fluid inlet arranged to supply the test solution to the test chamber such that the volume of chamber surrounding the iron saturation elements and at least one spacer is substantially filled by the test solution.

5. A test apparatus according to claim 1, wherein the iron saturation elements are formed from carbon steel.

6. A test apparatus according to claim 1, further comprising a second fluid inlet arranged to supply a test fluid to the test chamber.

7. A test apparatus according to claim 6, wherein the second fluid inlet is arranged to supply $H_2S$ or $CO_2$ to the test chamber.

8. A test apparatus according to claim 1, further comprising a support structure arranged to support at least two iron saturation elements and at least one spacer to form an iron saturation module.

9. A test apparatus according to claim 8, wherein the support structure is arranged to support a variable number of iron saturation elements and spacers so as to adjust the ratio of the volume of the test solution to the surface area of the iron saturation elements and the test sample exposed to the test solution.

10. A test apparatus according to claim 8, wherein at least two iron saturation elements are formed from a sheet material and have corresponding holes arranged to receive a guide rod of the support structure, and wherein the at least one spacer also comprises a hole arranged to receive the guide rod such that the spacer and the iron saturation elements are supported by the guide rod with the spacer between the iron saturation elements such that the test solution is in contact with first and second sides of the iron saturation elements surrounding the holes.

11. A method of testing a sample, the method comprising:
    receiving a test sample within a test chamber, the test chamber containing two or more iron saturation elements separated by a spacer; and
    filling the test chamber with a test solution, the iron saturation elements being arranged to saturate the test solution with iron;
    wherein each iron saturation element is shaped such that it has a predetermined surface area such that the ratio of the volume of the test solution to the surface area of the iron saturation elements and the test sample exposed to the test solution can be calculated.

* * * * *